(12) United States Patent
Lu et al.

(10) Patent No.: US 9,029,164 B2
(45) Date of Patent: May 12, 2015

(54) ANALYTICAL METHODS FOR ANALYZING AND DETERMINING IMPURITIES IN DIANHYDROGALACTITOL

(71) Applicant: Del Mar Pharmaceuticals, Vancouver (CA)

(72) Inventors: Xiaoyun Lu, Va (CA); Mike Tso-Ping Li, Cupertino, CA (US)

(73) Assignee: Del Mar Pharmaceuticals, Vancouver (CA)

(*) Notice: Subject to any disclaimer, the term of this patent is extended or adjusted under 35 U.S.C. 154(b) by 0 days.

(21) Appl. No.: 14/083,135

(22) Filed: Nov. 18, 2013

(65) Prior Publication Data

US 2014/0315318 A1    Oct. 23, 2014

Related U.S. Application Data

(63) Continuation-in-part of application No. 13/933,844, filed on Jul. 2, 2013, which is a continuation-in-part of application No. PCT/IB2013/000793, filed on Feb. 26, 2013.

(60) Provisional application No. 61/603,464, filed on Feb. 27, 2012.

(51) Int. Cl.
*G01N 33/15* (2006.01)
*G01N 21/49* (2006.01)
*G01N 30/88* (2006.01)

(52) U.S. Cl.
CPC ............... *G01N 33/15* (2013.01); *G01N 21/49* (2013.01); *G01N 30/88* (2013.01); *G01N 2030/8813* (2013.01); *G01N 2030/8872* (2013.01)

(58) Field of Classification Search
USPC ..................... 436/131, 93; 600/316; 424/649
See application file for complete search history.

(56) References Cited

U.S. PATENT DOCUMENTS 7,157,079 B2    1/2007  Nielsen et al.
8,563,758 B2*  10/2013  Brown .......................... 549/521

FOREIGN PATENT DOCUMENTS

WO    2012024368 A2    2/2012

OTHER PUBLICATIONS

R. N. Rao et al., "An Overview of the Recent Trends in Development of HPLC Methods for Determination of Impurities in Drugs," J. Pharm. Biomed. Analysis 33, (2003), pp. 335-377.
(Continued)

*Primary Examiner* — Rebecca M Fritchman
(74) *Attorney, Agent, or Firm* — Ditthavong Mori & Steiner, P.C.

(57) ABSTRACT

An improved analytical method for analysis of dianhydrogalactitol preparations provides a method for determining the purity of dianhydrogalactitol and detecting impurities in preparations of dianhydrogalactitol, as well as identifying any such impurities. The method employs high performance liquid chromatography (HPLC), in particular, HPLC with evaporative light scattering detection (ELSD); the HPLC can be followed by tandem mass spectroscopy. The method can further comprise the step of performing preparative HPLC collection of at least one specific substance peak present in a preparation of dianhydrogalactitol.

22 Claims, 8 Drawing Sheets

(56) References Cited

OTHER PUBLICATIONS

D. Bartos et al., "Recent Advances in the Impurity Profiling of Drugs," Curr. Pharm. Anal. 4, (2008), pp. 215-230.

M.D. Lantz et al., "Simultaneous Resolution and Detection of a Drug Substance, Impurities, and Counter Ion Using a Mixed-Mode HPLC Column with Evaporative Light Scattering Detection," J. Liquid Chromatography Rel. Tech. 20, (1997), pp. 1409-1422.

* cited by examiner

ANALYTICAL METHODS FOR ANALYZING AND DETERMINING IMPURITIES IN DIANHYDROGALACTITOL

CROSS-REFERENCES

This application claims the benefit and is a continuation-in-part of U.S. patent application Ser. No. 13/933,844, by Xiaoyun Lu, entitled "Improved Analytical Methods for Analyzing and Determining Impurities in Dianhydrogalactitol," and filed on Jul. 2, 2013, which in turn claims the benefit and is a continuation-in-part of PCT Application Serial No. PCT/IB2013/000793, by Xiaoyun Lu, entitled "Improved Analytical Methods for Analyzing and Determining Impurities in Dianhydrogalactitol," and filed on Feb. 26, 2013, designating the United States, which in turn, claims the benefit of U.S. Provisional Patent Application Ser. No. 61/603,464, entitled "Improved Analytical Methods for Analyzing and Determining Impurities in Dianhydrogalactitol" by Xiaoyun Lu, filed Feb. 27, 2012. The contents of both of these applications are incorporated herein in their entirety by this reference.

FIELD OF THE INVENTION

This invention is directed to improved analytical methods for dianhydrogalactitol, especially involving high performance liquid chromatography (HPLC).

BACKGROUND OF THE INVENTION

Dianhydrogalactitol (1,2:5,6 dianhydrogalactitol or DAG) is one of a number of hexitols or hexitol derivatives having significant pharmacological activity, including chemotherapeutic activity. In particular, dianhydrogalactitol has been suggested for use in chemotherapy, such as in U.S. Pat. No. 7,157,059 to Nielsen et al., incorporated herein by this reference.

Dianhydrogalactitol has activity against a number of neoplasms. However, if dianhydrogalactitol is to be used successfully as a therapeutic agent, an extremely high degree of purity and the removal of impurities is essential. The presence of impurities can lead to undesirable side effects. One example occurred a number of years ago, when impurities present in a batch of the amino acid tryptophan, a normal constituent of protein, were responsible for a significant outbreak of eosinophilia-myalgia syndrome, which caused a large number of cases of permanent disability and at least 37 deaths. This is particularly important if the therapeutic agent such as dianhydrogalactitol is to be employed in patients with compromised immune systems or liver or kidney dysfunction, or in elderly patients. Such patients may experience a greater incidence of undesirable side effects owing to their sensitivity to contaminants.

One of the impurities found in preparations of dianhydrogalactitol is dulcitol. Other impurities exist in preparations of dianhydrogalactitol as well, depending on their method of preparation.

Therefore, there is a need for improved analytical methods to detect impurities and degradation products in preparations of dianhydrogalactitol to provide preparations of greater purity that are less likely to induce side effects when dianhydrogalactitol is administered for therapeutic purposes.

SUMMARY OF THE INVENTION

An improved analytical method for determining the purity of dianhydrogalactitol and detecting impurities and degradation products in preparations of dianhydrogalactitol that meets these needs is described herein.

In general, this analytical method employs high performance liquid chromatography (HPLC), in particular, HPLC with refractive index (RI) detection.

In one alternative, an analytical method for analyzing the presence and quantity of impurities present in a preparation of dianhydrogalactitol comprises the steps of:

(1) analyzing a preparation of dianhydrogalactitol by subjecting the preparation to high performance liquid chromatography using elution with a mobile phase gradient to separate dianhydrogalactitol from dulcitol and other contaminants of the preparation; and (2) determining the relative concentration of one or more peaks resolved by high performance liquid chromatography that represent compounds other than dianhydrogalactitol itself.

The compounds other than dianhydrogalactitol itself can be at least one of: (1) dulcitol; (2) an impurity other than dulcitol; and (3) a degradation product of dianhydrogalactitol.

In one alternative of this method, elution is with a gradient of NaOH from about 2.5 mM to about 0.1 mM. Preferably, elution is with a gradient of NaOH from about 1.5 mM to about 0.1 mM. More preferably, elution is with a gradient of NaOH from about 1 mM to about 0.1 mM.

In another alternative of this method, elution is with a gradient of a combination of ammonium hydroxide and a volatile ammonium salt selected from the group consisting of ammonium formate and ammonium acetate and the total concentration of the ammonium formate and ammonium acetate is from about 2.5 mM to about 0.1 mM. Preferably, the total concentration of the ammonium hydroxide and the volatile ammonium salt selected from the group consisting of ammonium formate and ammonium acetate is from about 1.5 mM to about 0.1 mM. More preferably, the total concentration of the ammonium hydroxide and the volatile ammonium salt selected from the group consisting of ammonium formate and ammonium acetate is from about 1 mM to about 0.1 mM. Typically, the proportion of ammonium hydroxide and the volatile ammonium salt selected from the group consisting of ammonium formate and ammonium acetate is varied from about 100:1 at the beginning of elution to about 1:100 at the end of elution.

Typically, in this method, the step of determining the relative concentration of one or more peaks resolved by high performance liquid chromatography that represent compounds other than dianhydrogalactitol itself is performed by evaporative light scattering detection. Typically, the evaporative light scattering detection is compatible with electrospray LC/MS. Typically, the evaporative light scattering detection comprises post-column addition of a volatile solvent to enhance evaporation of the 100% aqueous mobile phase. Typically, the volatile solvent is selected from the group consisting of methanol, ethanol, isopropanol, and acetonitrile.

In one alternative, an electrospray tandem mass spectrometer is installed and connected on-line to an HPLC system with ELSD. Typically, in this alternative, mass spectral data providing chemical information for each of the impurities that may be present in a preparation of dianhydrogalactitol is collected. Also, typically, in this alternative, tandem mass spectral data providing structural information for each of the impurities that may be present in a preparation of dianhydrogalactitol is collected.

The method can further comprise the step of performing preparative HPLC collection of at least one specific substance peak present in a preparation of dianhydrogalactitol. The at last one substance peak present in the preparation of dianhydrogalactitol can be an impurity.

In another alternative, instead of gradient elution, isocratic elution can be used. When isocratic elution is used, in general, the method comprises the steps of:

(1) analyzing a preparation of dianhydrogalactitol by subjecting the preparation to high performance liquid chromatography using elution with an isocratic mobile phase to separate dianhydrogalactitol from dulcitol and other contaminants of the preparation; and (2) determining the relative concentration of one or more peaks resolved by high performance liquid chromatography that represent compounds other than dianhydrogalactitol itself.

In one alternative, when isocratic elution is used, the isocratic mobile phase is NaOH, and the concentration of NaOH is from about 5 mM to 0.1 mM. Preferably, the concentration of NaOH is from about 2.5 mM to about 0.1 mM. More preferably, the concentration of NaOH is about 1 mM.

In another alternative, when isocratic elution is used, the isocratic mobile phase is a combination of ammonium hydroxide and a volatile ammonium salt selected from the group consisting of ammonium formate and ammonium acetate and the total concentration of the ammonium hydroxide and the volatile ammonium salt selected from the group consisting of ammonium formate and ammonium acetate is from about 5 mM to 0.1 mM. Preferably, the total concentration of the ammonium hydroxide and the volatile ammonium acetate is from about 2.5 mM to about 0.1 mM. More preferably, the total concentration of the ammonium hydroxide and the volatile ammonium salt selected from the group consisting of ammonium formate and ammonium acetate is about 1 mM. Typically, the proportion of ammonium hydroxide and the volatile ammonium salt selected from the group consisting of ammonium formate and ammonium acetate is about 50:50.

Typically, in this alternative, the step of determining the relative concentration of one or more peaks resolved by high performance liquid chromatography that represent compounds other than dianhydrogalactitol itself is performed by evaporative light scattering detection (ELSD), as described above. Typically, the evaporative light scattering detection is compatible with electrospray LC/MS. Typically, the evaporative light scattering detection comprises post-column addition of a volatile solvent to enhance evaporation of the 100% aqueous mobile phase. Typically, the volatile solvent is selected from the group consisting of methanol, ethanol, isopropanol, and acetonitrile.

In this alternative as well, an electrospray tandem mass spectrometer can be installed and connected on-line to an HPLC system with ELSD. Typically, in this alternative, mass spectral data providing chemical information for each of the impurities that may be present in a preparation of dianhydrogalactitol is collected. Also, typically, in this alternative, tandem mass spectral data providing structural information for each of the impurities that may be present in a preparation of dianhydrogalactitol is collected.

This alternative of a method according to the present invention can further comprise the step of performing HPLC collection of at least one specific substance peak present in a preparation of dianhydrogalactitol. The at last one substance peak present in the preparation of dianhydrogalactitol can be an impurity.

In still another alternative, an analytical method for analyzing the presence and quantity of impurities present in a preparation of dianhydrogalactitol comprises the step of analyzing a preparation of dianhydrogalactitol by subjecting the preparation to high performance liquid chromatography (HPLC) on an HPLC column using elution with a mobile phase gradient to separate dianhydrogalactitol from dulcitol and other contaminants of the preparation; wherein the high performance liquid chromatography employs evaporative light scattering detection (ELSD).

Typically, the HPLC column is a silica gel column bonded to C18 compounds and finished with an endcapping procedure employing Lewis acid-Lewis base chemistry.

Typically, elution is performed with a gradient of 95% water/5% acetonitrile to 70% water/30% acetonitrile, returning to 95% water/5% acetonitrile. Typically, the time schedule for varying the eluant is as follows: 0 minutes, 95% water/5% acetonitrile; 15 minutes, 95% water/5% acetonitrile; 15.1 minutes, 70% water/30% acetonitrile; 20 minutes, 70% water/30% acetonitrile; 20.1 to 35 minutes, 95% water/5% acetonitrile. Typically, the method detects a monoepoxide degradation product of dianhydrogalactitol, a monoepoxide dimer, and dulcitol. Preferably, the method also detects a dimer of dianhydrogalactitol and condensed products.

Typically, the peaks resulting from HPLC are analyzed by LC-MS.

Typically, the method further comprises a step of determining the relative concentration of one or more peaks resolved by high performance liquid chromatography that represent compounds other than dianhydrogalactitol itself.

In an alternative for detection by ELSD, typically, the column temperature is about 30° C.

Typically, the flow rate is about 0.5 mL/min. Typically, the ELSD detector is operated in cooling mode with the drift tube temperature of 35° C. and gain 400, 2 pps, 45 PSI. Typically, in this alternative, Mobile Phase A and Mobile Phase B are employed, with Mobile Phase A being 0.05% formic acid in water and Mobile Phase B being 100% methanol. Typically, with these mobile phases, elution is performed from 0 minutes to 25 minutes with 100% of 0.05% formic acid in water, from 25 minutes to 25.1 minutes with 90% of 0.05% formic acid in water and 10% of 100% methanol, from 25.1 minutes to 35 minutes with 10% of 0.05% formic acid in water and 90% of 100% methanol, and from 35.1 minutes to 50 minutes with 100% of 0.05% formic acid in water.

The method can further comprise the preparation of an external calibration standard curve for an impurity. The impurity can be selected from the group consisting of dulcitol, a monoepoxide degradation product of dianhydrogalactitol, and a dimer of dianhydrogalactitol. The method can estimate the content of an unknown impurity by using a calibration standard curve established by chromatography of dianhydrogalactitol reference material.

Another alternative employing HPLC and ELSD employs a dual elution sequence. The dual elution sequence is as follows: a first part of the elution sequence in which elution is performed from 0 minutes to 25 minutes with 100% of 0.05% formic acid in water, from 25 minutes to 25.1 minutes with 90% of 0.05% formic acid in water and 10% of 100% methanol, from 25.1 minutes to 35 minutes with 10% of 0.05% formic acid in water and 90% of methanol, and from 35.1 minutes to 50 minutes with 100% of 0.05% formic acid in water, and a second part of the elution sequence in which elution is performed as follows: from 0 minutes to 7.5 minutes with 100% of 0.05% formic acid; from 7.5 minutes to 7.6 minutes with 97% of 0.05% formic acid and 3% of methanol; and from 7.6 minutes to 20 minutes with 100% of 0.05% formic acid. In this alternative, typically the column temperature for HPLC is about 30° C., the sample temperature for HPLC is about 5° C., the flow rate for HPLC is about 0.5 mL/min, and the injection volume is about 10-100 µL. In this alternative, typically, for ELSD, the gain is about 400, the drift tube temperature is about 45° C., the gas pressure is about 35 PSI of nitrogen, the nebulizer is set to cooling, the data rate is 2 points per second, and the Rayleigh factor is about 6.0. Typically, in this alternative, standards of dulcitol at 0.1, 0.08, 0.05, 0.03, 0.01, 0.005 mg/mL are employed to determine the sensitivity and linearity of the system. Typically, in this alternative, the retention time for dulcitol is about 6.4 minutes and the retention time for dianhydrogalactitol is about 12.1 minutes. In this alternative, the amount and percentage of a dulcitol impurity can be determined from the results of HPLC and ELSD. Also, in this alternative, the amount and percentage of an unknown impurity other than dulcitol can be determined from the results of HPLC and ELSD.

BRIEF DESCRIPTION OF THE DRAWINGS

These and other features, aspects, and advantages of the present invention will become better understood with reference to the following description, appended claims, and accompanying drawings where:

in FIG. 2, the dianhydrogalactitol-dulcitol standard is shown in the top panel, and the water blank is shown in the bottom panel.

DETAILED DESCRIPTION OF THE INVENTION

This invention is directed to improved analytical methods for determining the purity of dianhydrogalactitol and determining the existence and concentration of impurities present in preparations of dianhydrogalactitol.

The structure of dianhydrogalactitol is shown below in Formula (I).

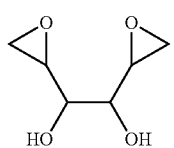

(I)

One of the significant impurities present in dianhydrogalactitol preparations is dulcitol. The structure of dulcitol is shown below in Formula (II). Other impurities are known to exist in dianhydrogalactitol preparations.

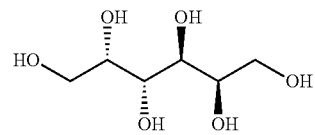

(II)

An improved method of analyzing dianhydrogalactitol preparations is based on HPLC (high performance liquid chromatography) with evaporative light scattering detection (ELSD). In one alternative, to detect and identify all significant components present in such dianhydrogalactitol preparations, HPLC is combined with mass spectroscopy (MS).

The theory and practice of HPLC are described in L. R. Snyder et al., "Introduction to Modern Liquid Chromatography" (3$^{rd}$ ed., John Wiley & Sons, New York, 2009). The theory and practice of MS are described in E. de Hoffmann & V. Stroobant, "Mass Spectroscopy: Principles and Applications" (3$^{rd}$ ed., John Wiley & Sons, New York, 2007).

Figure 1:
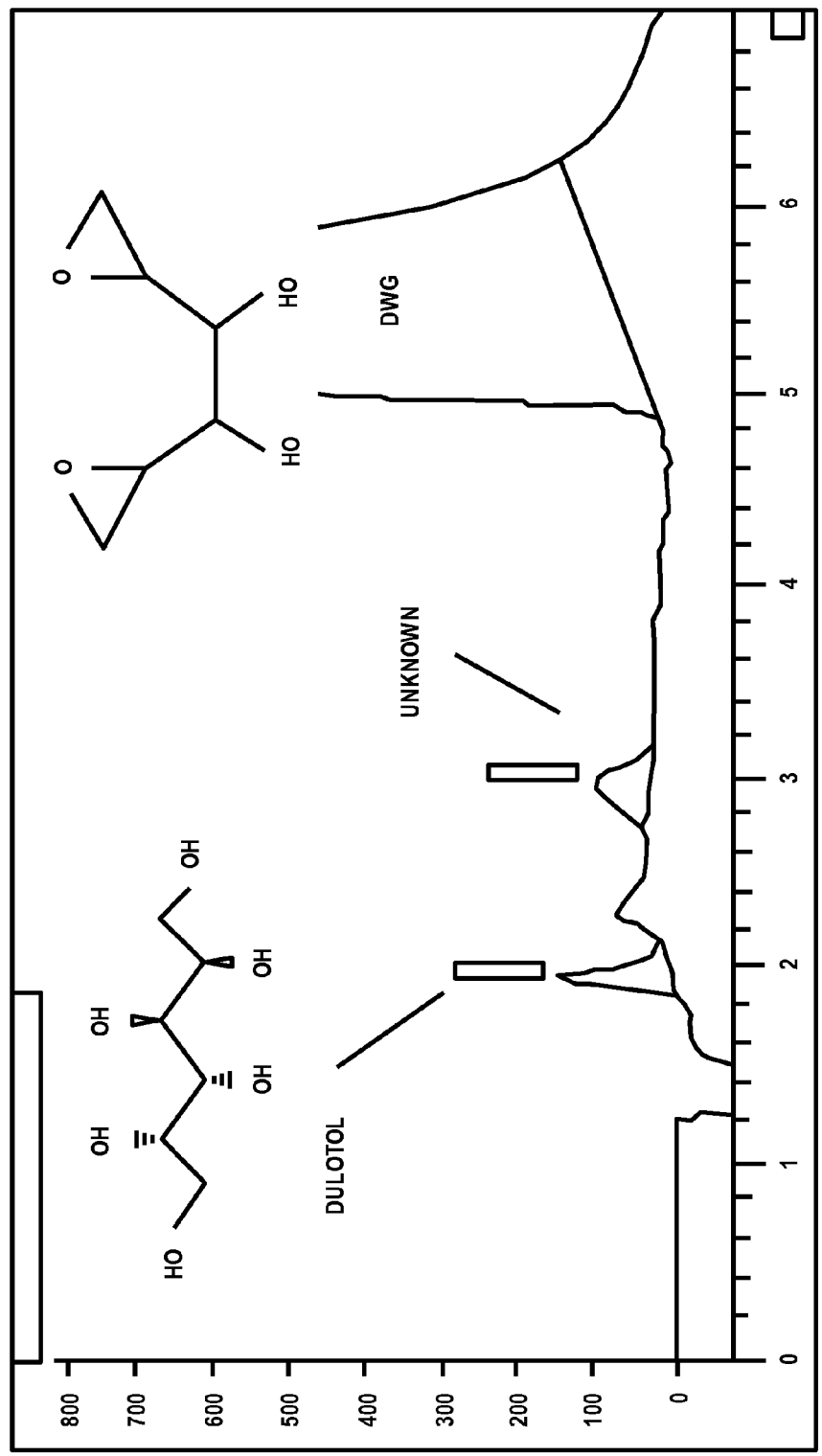
FIG. 1 is a representative HPLC/RI chromatogram of a preparation of dianhydrogalactitol, showing resolution of dulcitol and an unknown related substance at RRT~0.6 in the bulk drug and drug product.
Figure 2:
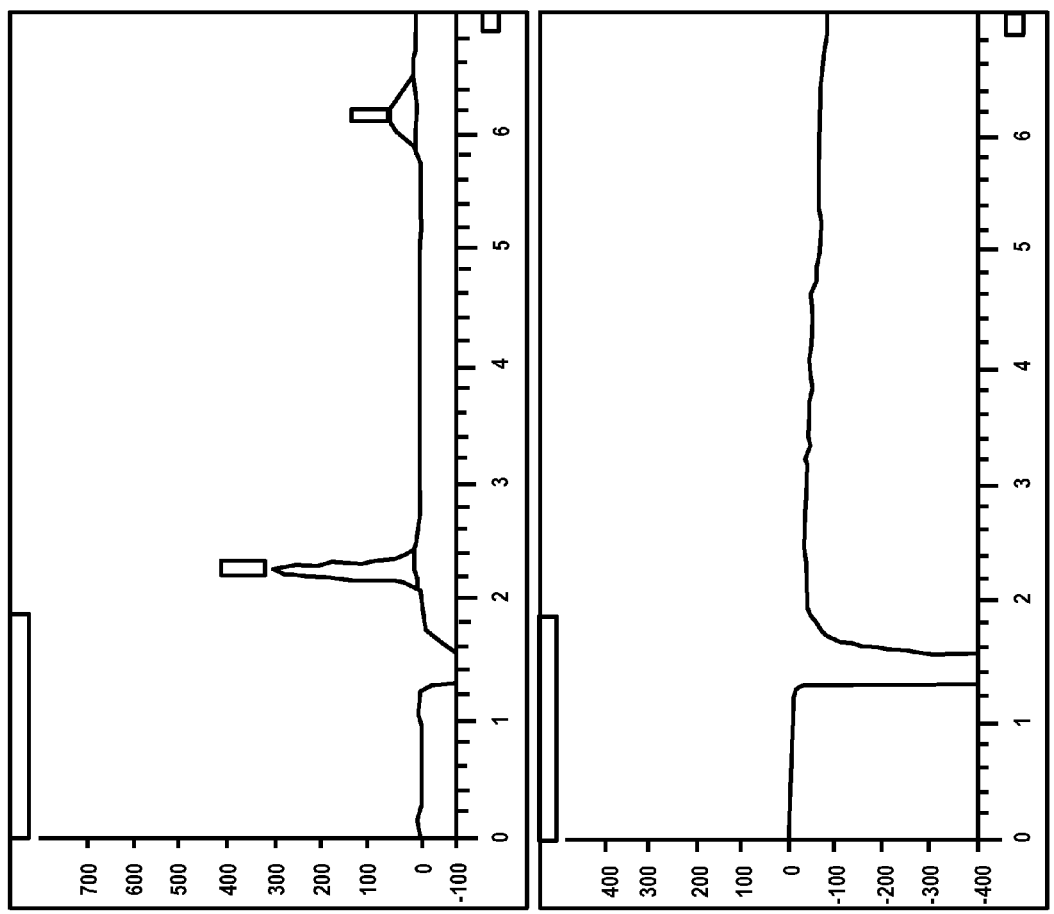
FIG. 2 shows representative HPLC chromatograms showing resolution of dianhydrogalactitol and dulcitol in a standard, and, for comparison, a water blank.

The HPLC method has demonstrated resolution of a synthetic intermediate, dulcitol, in preparations of dianhydrogalactitol, in addition to resolution of an unknown related substance observed at RRT 0.6 (FIG. 1). FIG. 1 is a representative HPLC/RI chromatogram of a preparation of dianhydrogalactitol, showing resolution of dulcitol and an unknown related substance at RRT~0.6 in the bulk drug and drug product. Representative HLPC chromatograms showing resolution of dianhydrogalactitol and dulcitol in a standard, and, for comparison, a water blank, are shown in FIG. 2. In FIG. 2, the dianhydrogalactitol-dulcitol standard is shown in the top panel, and the water blank is shown in the bottom panel.

The present application describes improved HPLC chromatographic conditions for resolution of potentially co-eluting substances. A thermally stressed dianhydrogalactitol product sample is evaluated to provide confirmation of the chromatographic conditions appropriate for resolution of dulcitol and other related impurities and degradation products. Subsequently, LC/MS and LC/MS/MS is performed to characterize the unknown DAG-related substance at RRT~0.6 to provide mass spectral characterization and determination of the chemical structure of this unidentified component.

Previously employed HPLC conditions involve isocratic elution of dianhydrogalactitol and its related substances using a 50 mM NaOH mobile phase. In an improvement on these conditions, employed as part of the method disclosed herein, a gradient mobile phase is employed. One alternative is the use of NaOH in a concentration gradient. If NaOH is employed in a concentration gradient, typically elution is with a gradient of NaOH from about 2.5 mM to about 0.1 mM. Preferably, elution is with a gradient of NaOH from about 1.5 mM to about 0.1 mM. More preferably, elution is with a gradient of NaOH from about 1 mM to about 0.1 mM.

In another alternative, a combination of ammonium hydroxide and a volatile ammonium salt selected from the group consisting of ammonium formate and ammonium acetate can be used as eluant. In this alternative, the total concentration of the ammonium formate and ammonium acetate is from about 2.5 mM to about 0.1 mM. Preferably, the total concentration of the ammonium hydroxide and the volatile ammonium salt selected from the group consisting of ammonium formate and ammonium acetate is from about 1.5 mM to about 0.1 mM. More preferably, the total concentration of the ammonium hydroxide and the volatile ammonium salt selected from the group consisting of ammonium formate and ammonium acetate is from about 1 mM to about 0.1 mM.

Typically, the proportion of ammonium hydroxide and the volatile ammonium salt selected from the group consisting of ammonium formate and ammonium acetate is varied from about 100:1 at the beginning of elution to about 1:100 at the end of elution.

Other gradient elution schemes are known in the art.

Typically, in HPLC analytical methods according to the present invention, detection is by means of evaporative light scattering (ELSD). An evaporative light scattering detector (ELSD) atomizes the column eluate, shines light on the resulting particulate components, and detects the resulting scattered light. Theoretically, an ELSD can detect any non-volatile component. The evaporative light scattering detection of a non-chromogenic compound is based on nebulization of the HPLC eluant and evaporation of mobile-phase solvents to produce atomizing solute particles for light scattering detection. This nebulization and solvent evaporation process to produce atomizing analyte solute particles is comparable to the electrospray LC/MS procedure. Typically, the ELSD detection is compatible with electrospray LC/MS.

Implementation of an HPC method with ELSD detection that is compatible with electrospray LC/MS application involves post-column addition of a volatile solvent to enhance evaporation of the 100% aqueous mobile phase. The volatile solvent is typically selected from the group consisting of methanol, ethanol, isopropanol, and acetonitrile.

Accordingly, in methods according to the present invention, an electrospray tandem mass spectrometer is installed and connected on-line to an HPLC system with ELSD. Mass spectral data providing molecular information and tandem mass spectral data providing chemical structural information for each of the impurities that may be present in a preparation of dianhydrogalactitol can be collected. Mass spectroscopy in tandem with HPLC will provide molecular ion information and possible chemical structures having a molecular weight consistent with the molecular ion information for each of the observed impurities and degradation products.

In another alternative, preparative HPLC collection of specific DAG-related substance peaks, including impurities present in a preparation of DAG, can be performed.

Accordingly, one analytical method for analyzing the presence and quantity of impurities present in a preparation of dianhydrogalactitol comprises the steps of:

(1) analyzing a preparation of dianhydrogalactitol by subjecting the preparation to high performance liquid chromatography using elution with a mobile phase gradient to separate dianhydrogalactitol from dulcitol and other contaminants of the preparation; and (2) determining the relative concentration of one or more peaks resolved by high performance liquid chromatography that represent compounds other than dianhydrogalactitol itself.

The compounds other than dianhydrogalactitol itself can be at least one of: (1) dulcitol; (2) an impurity other than dulcitol; and (3) a degradation product of dianhydrogalactitol.

Typically, in one alternative, in this method, the mobile phase gradient is a gradient of sodium hydroxide.

In another alternative, in this method, the mobile phase gradient is a gradient of a combination of ammonium hydroxide and a volatile ammonium salt selected from the group consisting of ammonium formate and ammonium acetate.

Typically, in this method, detection is by evaporative light scattering. Typically, when evaporative light scattering is employed, the method further comprises the step of post-column addition of a volatile solvent to enhance evaporation of components of the mobile phase.

Typically, the present invention further comprises the step of analyzing one or more peaks eluting from the high performance liquid chromatography by electrospray tandem mass spectroscopy.

In one alternative, the present invention further comprises the step of preparative HPLC collection of at least one specific DAG-related substance peak.

If an impurity or degradation product (other than dulcitol) exists, the unknown impurity or degradation product can be identified by separation by column chromatography followed by at least one purification procedure to yield a solid unknown sample which can then be characterized for identification by at least one standard analytical procedure selected from the group consisting of nuclear magnetic resonance (NMR), mass spectroscopy (MS), Fourier transform infrared spectroscopy (FT-IR), elemental analysis, determination of purity by HPLC, and determination of water content by the Karl Fischer titration method. These methods are well known in the art.

In another alternative, the method comprises:

(1) analyzing a preparation of dianhydrogalactitol by subjecting the preparation to high performance liquid chromatography using elution with an isocratic mobile phase to separate dianhydrogalactitol from dulcitol and other contaminants of the preparation; and (2) determining the relative concentration of one or more peaks resolved by high performance liquid chromatography that represent compounds other than dianhydrogalactitol itself.

As in the method employing gradient elution, the compounds other than dianhydrogalactitol itself can be at least one of: (1) dulcitol; (2) an impurity other than dulcitol; and (3) a degradation product of dianhydrogalactitol.

In this alternative, the elution with the isocratic mobile phase can either be elution with sodium hydroxide or elution with a combination of ammonium hydroxide and a volatile ammonium salt selected from the group consisting of ammonium formate and ammonium acetate. If the isocratic mobile phase is sodium hydroxide, typically, the concentration of NaOH is from about 5 mM to 0.1 mM. Preferably, the concentration of NaOH is from about 2.5 mM to about 0.1 mM. More preferably, the concentration of NaOH is about 1 mM. If the isocratic mobile phase is a combination of ammonium hydroxide and a volatile ammonium salt selected from the group consisting of ammonium formate and ammonium acetate, the total concentration of the ammonium hydroxide and the volatile ammonium salt selected from the group consisting of ammonium formate and ammonium acetate is from about 5 mM to 0.1 mM. Preferably, the total concentration of the ammonium hydroxide and the volatile ammonium acetate is from about 2.5 mM to about 0.1 mM. More preferably, the total concentration of the ammonium hydroxide and the volatile ammonium salt selected from the group consisting of ammonium formate and ammonium acetate is about 1 mM. Typically, the proportion of ammonium hydroxide and the volatile ammonium salt selected from the group consisting of ammonium formate and ammonium acetate is about 50:50.

In an alternative method to improve resolution, an evaporative light scattering detector (ELSD) is employed employing altered elution conditions. Typically, in this method, the HPLC column is a silica gel column bonded to C18 compounds and finished with an endcapping procedure employing Lewis acid-Lewis base chemistry such as the YMC C18 column. Typically, elution is performed with a gradient of 95% water/5% acetonitrile to 70% water/30% acetonitrile, returning to 95% water/5% acetonitrile. Preferably, the time schedule for varying the eluant is as follows: 0 minutes, 95% water/5% acetonitrile; 15 minutes, 95% water/5% acetonitrile; 15.1 minutes, 70% water/30% acetonitrile; 20 minutes, 70% water/30% acetonitrile; 20.1 to 35 minutes, 95% water/5% acetonitrile. Preferably, the HPLC method detects a monoepoxide degradation product of dianhydrogalactitol, a monoepoxide dimer, and dulcitol. More preferably, the HPLC method also detects a dimer of dianhydrogalactitol and condensed products.

Preferably, in this alternative of the method, the peaks resulting from HPLC are analyzed by LC-MS.

In another alternative method, as shown in Example 3, an Atlantis HPLC column is employed. Typically, in this method, the column temperature is about 30° C. Typically, in this method, the flow rate is about 0.5 mL/min. Typically, in this method, the injection volume is about 10 µL to about 100 µL. Typically, in this method, an ELSD detector is used. Typically, in this method, the ELSD detector is operated in cooling mode with the drift tube temperature of 35° C. and gain 400, 2 pps, 45 PSI. Typically, in this method, Mobile Phase A and Mobile Phase B are employed, with Mobile Phase A being 0.05% formic acid in water and Mobile Phase B being 100% methanol. Typically, in this method, elution is performed from 0 minutes to 25 minutes with 100% of 0.05% formic acid in water, from 25 minutes to 25.1 minutes with 90% of 0.05% formic acid in water and 10% of 100% methanol, from 25.1 minutes to 35 minutes with 10% of 0.05% formic acid in water and 90% of 100% methanol, and from 35.1 minutes to 50 minutes with 100% of 0.05% formic acid in water.

Typically, this alternative of the method further comprises the preparation of an external calibration standard curve for an impurity. The impurity can be, but is not limited to, an impurity selected from the group consisting of dulcitol, a monoepoxide degradation product of dianhydrogalactitol, and a dimer of dianhydrogalactitol. In this method, for an unknown impurity, the content of the unknown impurity can be estimated using a calibration standard curve established by chromatography of dianhydrogalactitol reference material.

In another alternative, as shown in Example 4, following the elution sequence described above, namely where elution is performed from 0 minutes to 25 minutes with 100% of 0.05% formic acid in water, from 25 minutes to 25.1 minutes with 90% of 0.05% formic acid in water and 10% of 100% methanol, from 25.1 minutes to 35 minutes with 10% of 0.05% formic acid in water and 90% of 100% methanol, and from 35.1 minutes to 50 minutes with 100% of 0.05% formic acid in water, an additional elution sequence is performed as follows: from 0 minutes to 7.5 minutes with 100% of 0.05% formic acid; from 7.5 minutes to 7.6 minutes with 97% of 0.05% formic acid and 3% of methanol; and from 7.6 minutes to 20 minutes with 100% of 0.05% formic acid. In this alternative, typically the column temperature for HPLC is about 30° C., the sample temperature for HPLC is about 5° C., the flow rate for HPLC is about 0.5 mL/min, and the injection volume is about 100 µL. In this alternative, typically, for ELSD, the gain is about 400, the drift tube temperature is about 45° C., the gas pressure is about 35 PSI of nitrogen, the nebulizer is set to cooling, the data rate is 2 points per second, and the Rayleigh factor is about 6.0. Typically, in this alternative, standards of dulcitol at 0.005 to 0.1 mg/mL are employed to determine the sensitivity and linearity of the system. Typically, in this alternative, the retention time for dulcitol is about 6.4 minutes and the retention time for dianhydrogalactitol is about 12.1 minutes. In this alternative, the amount and percentage of a dulcitol impurity can be determined from the results of HPLC and ELSD. Also, in this alternative, the amount and percentage of an unknown impurity other than dulcitol can be determined from the results of HPLC and ELSD.

The invention is illustrated by the following Examples. These examples are for illustrative purposes only, and are not intended to limit the invention.

EXAMPLES

Example 1

HPLC Analysis of Dianhydrogalactitol Preparations Employing Isocratic Sodium Hydroxide Elution The procedure described in this Example is used for determining dulcitol and related impurities in a dianhydrogalactitol drug preparation by ion exchange high performance liquid chromatography with refractive index detection.

In this procedure, the samples are prepared with dianhydrogalactitol at a target concentration of 5 mg/mL. Dulcitol, dianhydrogalactitol, and related impurities are separated using an anion exchange column (Hamilton RCX-10, 250×4.1 mm, 7 µm), with 50 mM NaOH as isocratic mobile phase with refractive index detection. Dulcitol concentration is determined with an external reference standard and the contents of related substances are estimated using a DAG reference standard.

A suitable HPLC system and data acquisition system is an Agilent Technologies 1200 Series HPLC system or equivalent equipped with the following: Quat pump, Model G1311A or equivalent; auto sampler, Model 1329A or equivalent; RID detector, Model 1362A or equivalent; column temperature controller capable of 30±3° C.; and degasser, Model G1322 or equivalent. The column is a Hamilton RCX anion exchange column 250×4.1-mm, 7 µm, P/N 79440, or equivalent. Data acquisition is performed by a ChemStation and ChemStore Client/Server or an equivalent data system.

The following chemicals are used. Water is Milli-Q water or deionized water. Sodium hydroxide is standard purified grade. Dulcitol and DAG reference standards are of purity >98.0%.

For the mobile phase (50 mM NaOH), 2.0 g NaOH is dissolved in 1 liter of water. The solution is filtered through an 0.45-µm filter. The mobile phase can be stored up to 1 month at room temperature. For the dulcitol reference stock solution (nominal 500 µg/mL), 25 mg of dulcitol reference standard is accurately weighed into a 50-mL volumetric flask. The dulcitol is diluted to volume with deionized water and mixed well. The prepared stock solution can be stored up to 3 days at 2-8° C. For the DAG reference stock solution (nominal 500 µg/mL), 25 mg of DAG reference standard is accurately weighed into a 50-mL volumetric flask. The DAG is diluted to volume with deionized water and mixed well. The prepared stock solution can be stored up to 3 days at 2-8° C. For the dulcitol-DAG standard solution (dulcitol 50 µg/mL+DAG 50 µg/mL; each at 1% of 5 mg/mL DAG), 1.0 ml of dulcitol stock and 1.0 ml of DAG stock are each quantitatively transferred into a 10-mL volumetric flask, diluted to volume with water and mixed well.

For DAG sample preparation from an API sample (nominal 1 mg/mL), about 25 mg of API sample of DAG is accurately weighed in a clean 25-mL volumetric flask. The DAG API sample is dissolved in approximately 5 mL of deionized water, diluted to volume with deionized water, and mixed. An aliquot of 1 to 2 mL of the test sample is transferred into an HPLC vial. Prepared samples can be stored for up to 2 days at 2-8° C.

For DAG sample preparation (nominal 5 mg/mL) for an API sample, about 50 mg of the API sample is accurately weighed into a clean 10-mL volumetric flask. The DAG API sample is dissolved in approximately 5 mL of water, diluted to volume with water, and mixed.

For DAG sample preparation from a lyophilized (40 mg/vial) sample, the sample is removed from the refrigerator in which the sample is stored and the seal removed. A volume of water of 5.0 mL is quantitatively transferred and the solution is mixed to dissolve the DAG, yielding an 8 mg/mL solution. An aliquot of 1.0 g of the reconstituted solution is diluted to 8.0 g with deionized water and mixed. A further aliquot of 1 to 2 mL of the test sample is transferred into an HPLC vial. Prepared samples can be stored for up to 2 days at 2-8° C.

For DAG sample preparation (nominal 5 mg/mL) for the drug product using lyophilized powder (40 mg/vial), the closure of the vial is cleaned and removed. The lyophilized vial is reconstituted with 8.0 mL water to yield a 5 mg/mL solution. An aliquot of 1 to 2 mL is transferred to an HPLC vial. Samples are prepared in duplicate (using two vials). Prepared samples can be stored at 2-8° C. for up to 24 hours.

For HPLC analysis, the HPLC system is turned on and the detector is allowed to warm up for at least 20 minutes. If necessary, place the HPLC mobile phase prepared as described above into the appropriate solvent inlet. The solvent line is primed with the mobile phase. The system and the column are equilibrated with HPLC mobile phase at a flow rate of 1.5 mL/min for at least 30 minutes. A sample analysis sequence is created. Once system suitability has been confirmed, a water blank is injected followed by injections of the standards and then the samples. A dulcitol-DAG standard is inserted after every 10 injections of samples and then a last bracketing standard at the end of the run. A suitable sample analysis sequence is shown in Table

TABLE 1

Sample Analysis Sequence

| Description | No. of Injections |
|---|---|
| Blank (100% water) | 1 |
| System Suitability Test, Dul-DAG Standard (50 µg/mL each) | 6 |
| Blank (100% water) | 1 |
| Test Samples (DAG drug substance and/or drug product) - assay (duplicate preparations) | 2 (n ≤ 20) |
| Bracketing Standard, Dul-DAG Standard (50 µg/mL each) | 2 |
| Blank (water) | 1 |

The samples are analyzed using RID. As indicated above, a suitable column is a Hamilton RCX ion exchange column (250×4.1 mm, 7 µm), P/N 79440 or equivalent. The mobile phase is 50 mM NaOH in deionized water (isocratic elution). The flow rate is 1.5 mL/min. The column temperature is 30° C. The injection volume is 50 µL. Detection is by RID at 35° C. The run time is 8 minutes.

For analysis and integration of the chromatograms, the HPLC software is used. The chromatograms for the blank, the samples, and the test standards are reviewed and compared. Manual integration and assignment of some peaks may be necessary. Integration parameters such as slope sensitivity, peak width, peak height threshold value for rejection, integration type of shoulder peak, baseline, and split peak, as well as other parameters, are adjusted to obtain appropriate integration and values for these parameters are recorded and applied to all samples and standards.

Suitability of the system is assessed as follows. The six replicated injections of the dulcitol-DAG standard solution are evaluated using the chromatographic performance requirements of Table 2.

TABLE 2

| Chromatographic Performance Requirements | |
|---|---|
| Dulcitol Retention time (RT): | ~2 min. |
| DAG Retention time (RT): | ~6 min. |
| Area Response variation % RSD: | ≤10.0% |
| Retention time variation % RSD: | ≤2.0% |

The dulcitol and DAG peak area in the bracketing standard solution injections should be 80% to 120% of the average peak area of each in previous SST injections. In case one bracketing standard fails to meet the criterion, the samples analyzed after the final passing bracketing standard should be re-analyzed.

In the analysis of the data, relative peak area=(peak area/total peak area)×100, where "peak area" is the individual peak area and "total peak area" is the sum of peak areas from all peaks.

Dulcitol concentration is calculated as indicated: Dulcitol ($C_u$, µg/mL)=$C_s$×mean sample peak area/mean dulcitol peak area of Dul-DAG standard injections, where $C_s$ is dulcitol concentration in µg/mL.

Dulcitol content (wt %) in DAG drug substance or drug product is calculated as indicated: Dulcitol wt %=$C_u$ (µg/mL)/1000/SC (mg/mL)×100%, where $C_u$ is dulcitol concentration (µg/mL) calculated as above, and SC is sample concentration (mg/mL) as prepared for drug substance or drug product. If dulcitol is present, the weight percent of dulcitol is reported if equal to or greater than 0.05%; it is reported to the nearest 0.01%.

If an unknown or previously unidentified impurity other than dulcitol is present in the DAG preparation, its concentration is calculated as follows: Unknown impurity concentration (µg/mL)=$C_s$×mean sample peak area/mean DAG peak area of Dul-DAG standard injections. If present, the unknown impurity weight percent is calculated as follows: $C_u$ (µg/mL)/1000/SC (mg/mL)×100%, where $C_u$=unknown concentration (µg/mL) calculated as above, and SC=sample concentration (mg/mL) as prepared in [0077] for drug substance or [0079] for drug product. Each unknown impurity, if present, is reported if equal to or greater than 0.05%; it is reported to the nearest 0.01%.

The assay results in weight percent are calculated for each sample and for the mean of duplicate samples.

Example 2

HPLC Analysis Employing Evaporative Light Scattering Detector Using Gradient of Water/Acetonitrile To improve resolution of impurities, another method of HPLC analysis was employed using an evaporative light scattering detector (ELSD) with a gradient of water/acetonitrile as detailed below.

Due to the limitations of the refractive index (RI) detector, the HPLC/RI method does not have sufficient specificity to obtain reliable impurity profile data, which pose the risks of exposure of patients to unacceptable levels of impurities that are unknown or are incompletely characterized. To address this concern, a more sensitive detector, such as the evaporative light scattering detector (ELSD) manufactured by Agilent, is used in conjunction with HPLC system for determination of impurities found in dianhydrogalactitol drug substance or drug product.

For example, a DAG sample was analyzed by HPLC/ELSD method using a YMC C18 column with the gradient shown in Table 3:

TABLE 3

| Time (min) | % water | % acetonitrile |
|---|---|---|
| 0 | 95 | 5 |
| 15 | 95 | 5 |
| 15.1 | 70 | 30 |
| 20 | 70 | 30 |
| 20.1 to 35 | 95 | 5 |

Figure 3:
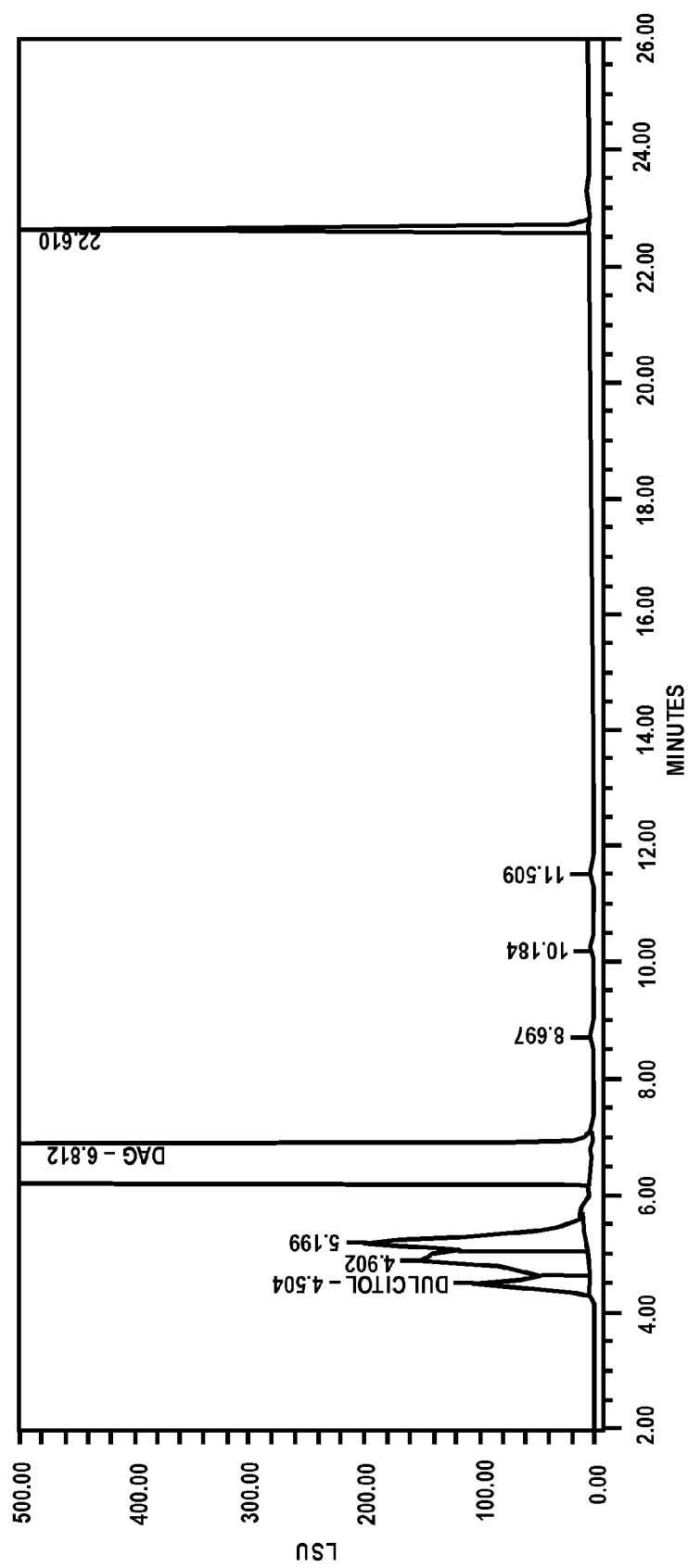
FIG. 3 is a HPLC chromatogram of a dianhydrogalactitol clinical sample using an evaporative light scattering detector for detection showing the existence of a possible dianhydrogalactitol dimer and possible condensed products, along with the monoepoxide and dulcitol as degradation products.
Figure 4:
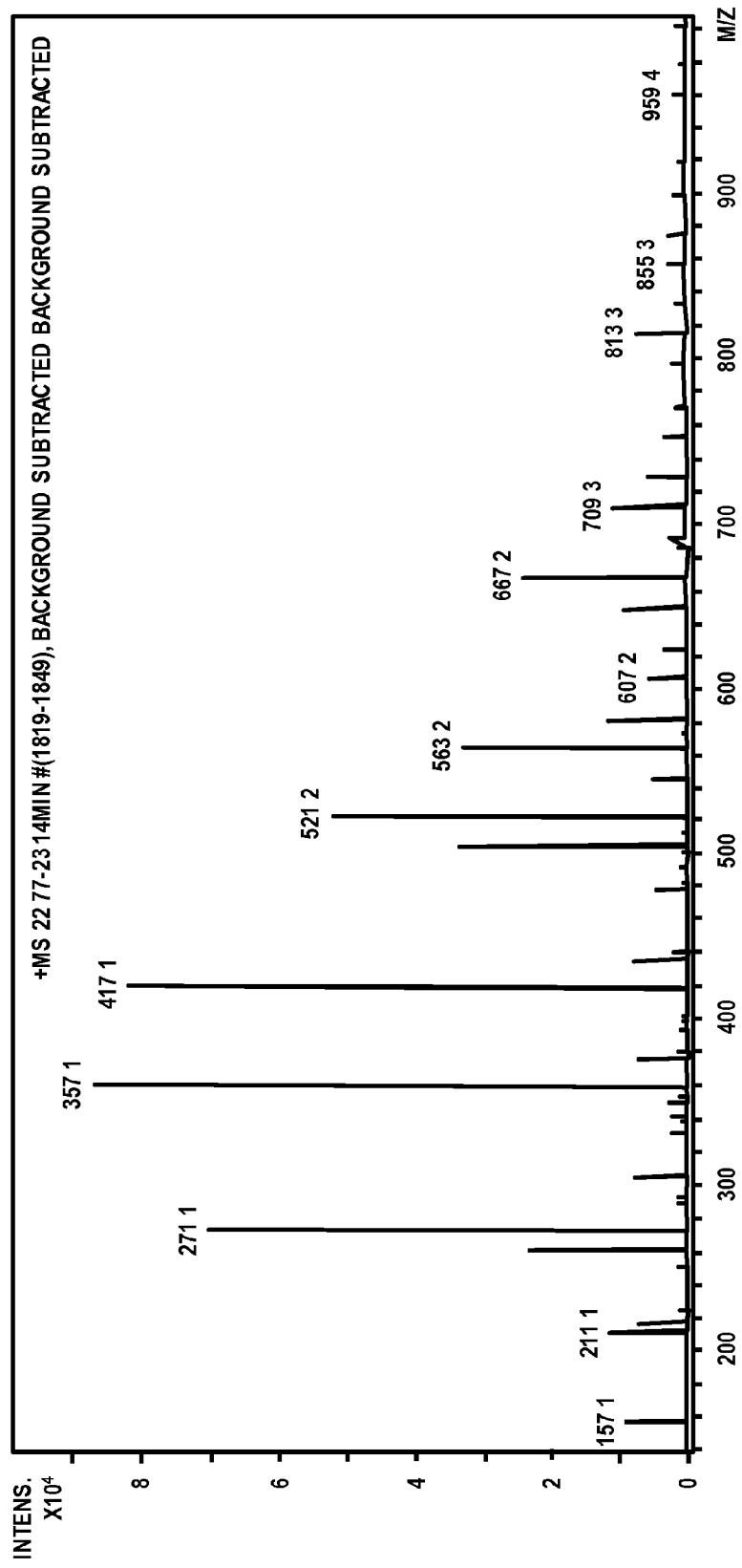
FIG. 4 is a mass spectroscopy profile of the impurity peak occurring at 22.6 minutes of the HPLC chromatogram of FIG. 3.

As shown in the chromatogram (FIG. 3), dulcitol was eluted at retention time of 4.5 minutes. The peaks eluted right after dulcitol were identified to be mono-epoxide related compounds, as supported by LC-MS data summarized in Table 4. The peak observed at 11.46 minutes is possibly DAG dimer and the peak eluted at 22.6 minutes contributed multiple peaks in LC-MS with m/z of 271, 357, 417, 512, and other peaks, which might be condensed products (FIG. 4). These data are consistent with the impurity profile expected by previous studies. As expected, the monoepoxide and dulcitol are two major degradation products obtained by this method.

TABLE 4

| RT (min) | % Area | Base peak m/z* | m/z | Comments |
|---|---|---|---|---|
| 4.55 | 1.22 | [M + Na]$^+$ = 205.1 | 182 | dulcitol |
| 4.92 | 2.68 | [M + Na]$^+$ = 351.1 | 328 | Mono-epoxide dimer |
|  |  |  | 187 | Mono-epoxide Na adduct |
| 5.21 | 2.31 | [M + Na]$^+$ = 187.1 | 164 | Mono-epoxide |
| 6.81 | 91.35 | [M + Na]$^+$ = 169.1 | 146 | DAG |
| 11.46 | 0.22 | [M + Na]$^+$ = 289.1 | 266 | DAG dimer |
| 22.61 | 2.22 | 271, 357, 417, 521 |  | Condensed products |

Example 3

HPLC Analysis with Formic Acid in Water/Methanol Gradient to Improve Resolution of Mono-Epoxide Peaks To improve the resolution of mono-epoxide peaks, a new method was developed. This new method employed the following parameters: The column was Atlantis C18, 250×4.6 mm, 5 μm. The column temperature was 30° C. The flow rate was 0.5 mL/min. The injection volume was 100 μL. The ELSD detector was operated in cooling mode with the drift tube temperature of 35° C. and gain 400, 2 pps, 45 PSI. Mobile Phase A was 0.05% formic acid in water. Mobile Phase B was 100% methanol. The gradient was shown in Table 5:

TABLE 5

| Time, min | % A | % B |
|---|---|---|
| 0 | 100 | 0 |
| 25 | 90 | 10 |
| 25.1-35 | 10 | 90 |
| 35.1-50 | 100 | 0 |

Figure 5:
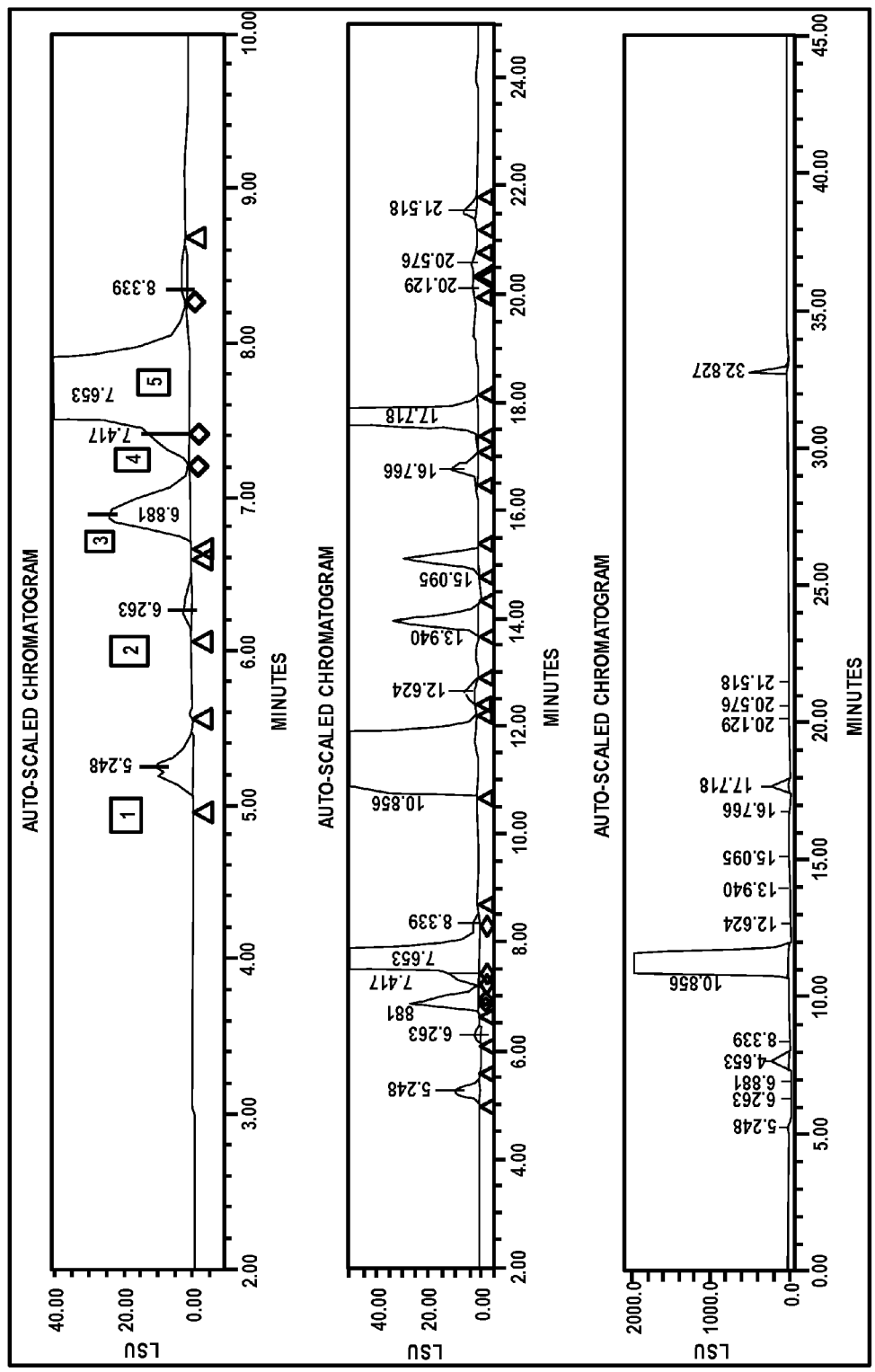
FIG. 5 is a chromatogram of a sample of dianhydrogalactitol as performed in Example 3 employing 0.05% formic acid in water as Mobile Phase A and 100% methanol as Mobile Phase B.

Better resolution of the early eluting impurities has been observed (refer to chromatogram of DAG sample below in FIG. 5). Dulcitol labeled peak 2 was eluted at retention time of 6.26 minutes or relative retention time (RRT) of 0.59. Dianhydrogalactitol was eluted at 10.86 minutes.

Since ELSD response is not linear, an external calibration standard curve is required for a known impurity, such as dulcitol, to determine the impurity content in a dianhydrogalactitol sample tested. For an unknown impurity contained in a sample of dianhydrogalactitol, the unknown impurity content can be estimated using a calibration standard curve established by chromatography of dianhydrogalactitol reference material.

Example 4

Further Improved Method for Detection or Determination of Impurities Employing Dual-Gradient HPLC Elution A further improved analytical method for the detection or determination of impurities in dianhydrogalactitol employs HPLC and ELSD with dual-gradient elution in HPLC. This method is described below.

In this analytical method, the following materials and equipment are used: an Atlantis C18, 250×4.6-mm, 5 μm HPLC column; a quaternary or binary HPLC pump; an Evaporative Light Scattering Detector (ELSD); an integrator or computer-based analytical system; a calibrated analytical balance; and Class A volumetric flasks and pipettes. The following reagents and standards are used: a dulcitol reference standard as described above; HPLC grade water; HPLC grade or equivalent formic acid (FA); HPLC grade or equivalent acetonitrile (ACN); and HPLC grade or equivalent methanol (MeOH).

For solutions that are employed in the method, the volume may be scaled to suit the needs of the analysis. It is important that all mobile phases are filtered. The sintered glass in the filtration apparatus may be a source of buffers that may interfere with sensitivity in the ELSD. All filtration apparatus should be rinsed thoroughly with Milli-Q grade water. To perform this, approximately 500 mL of Milli-Q grade water is filtered through the filtration apparatus. The water is discarded and the mobile phase is then filtered.

Test solution preparations are to be made in a fume hood using appropriate PPE (gloves, lab coat, and safety glasses). Test solution preparations are to be stored in a fume hood for disposal and are to be labelled appropriately.

Mobile Phase A is prepared by pipetting 0.5 mL of formic acid into 1000 mL of water and mixing well. The Mobile Phase A is filtered and degassed.

Mobile Phase B is MeOH. The Mobile Phase B is filtered and degassed.

Diluent A is water. Diluent B is prepared by mixing 20 mL of ACN with 180 mL of water and mixing well.

The standard and sample solution preparation is described below. The blank solution is water. The dulcitol stock solution is prepared by accurately transferring 100 mg of dulcitol reference standard to a 20-mL volumetric flask. About 15 mL of Diluent B is added and sonicated to dissolve. The solution is allowed to cool down to room temperature and diluted to volume with Diluent B and mixed well (5 mg/mL). The following standard solutions are prepared: 0.2, 0.1, 0.08, 0.05, 0.03, 0.01 and 0.005 mg/mL (system sensitivity solution). A 4.0% standard solution is prepared by pipetting 2.0 mL of dulcitol stock solution into a 50-mL volumetric flask. The solution is diluted to volume with water and mixed well (0.2 mg/mL). A 2.0% standard solution is prepared by pipetting 5.0 mL of 4.0% standard solution into a 10-mL volumetric flask. The solution is diluted to volume with water and mixed well (0.10 mg/mL). A 1.6% standard solution is prepared by pipetting 4.0 mL of 4.0% standard solution into a 10-mL volumetric flask. The solution is diluted to volume with water and mixed well (0.08 mg/mL). A 1.0% standard solution is prepared by pipetting 2.5 mL of 4.0% standard solution into a 10-mL volumetric flask. The solution is diluted to volume with water and mixed well (0.05 mg/mL). An 0.60% standard solution is prepared by pipetting 3.0 mL of 4.0% standard solution into a 20-mL volumetric flask. The solution is diluted to volume with water and mixed well (0.30 mg/mL). An 0.20% standard solution is prepared by pipetting 1.0 mL of 4.0% standard solution into a 20-mL volumetric flask. The solution is diluted to volume with water and mixed well (0.01 mg/mL). An 0.10% standard solution (system sensitivity solution) is prepared by pipetting 5.0 mL of 0.20% standard solution into a 10-mL volumetric flask. The solution is diluted to volume with water and mixed well (0.005 mg/mL).

Test sample working solutions are to be prepared in duplicate (A and B). Sample solutions must be prepared just before analysis. Sample injections must be performed within 15 minutes of sample solution preparation. Sample dilution may be required, in some cases, to quantitate any impurities that are overloaded.

For sample preparation, approximately 50 mg of test sample is accurately transferred into a 10-mL volumetric flask. The test sample is dissolved in water and diluted to volume and mixed well (5 mg/mL).

The HPLC operating conditions are as follows: The column is the Atlantis C18 250×4.6-mm, 5 μm HPLC column. Mobile Phase A is 0.05% FA in water. Mobile Phase B is MeOH. Gradients A and B are described below in Table 6. The column temperature is 30° C. The sample temperature is 5° C. The flow rate is 0.5 mL/min. The injection volume is 100 μL. The run time is 50 minutes for Gradient A and 20 minutes for Gradient B.

TABLE 6

|  | Time, mins | % A | % B |
| --- | --- | --- | --- |
| Gradient A | 0 | 100 | 0 |
|  | 25 | 90 | 10 |
|  | 25.1 | 10 | 90 |
|  | 35 | 10 | 90 |
|  | 35.1 | 100 | 0 |
|  | 50 | 100 | 0 |
| Gradient B | 0 | 100 | 0 |
|  | 7.5 | 97 | 3 |
|  | 7.6 | 100 | 0 |
|  | 20 | 100 | 0 |

The ELSD operating conditions are as follows: The gain is 400. The drift tube temperature is 45° C. The gas pressure (nitrogen) is 35 PSI. The nebulizer is set to cooling. The data rate is 2 points per second. The Rayleigh factor, set directly in the detector, is 6.0.

The injection sequence is shown in Table 7. Blank injections are to be repeated until a stable and reproducible baseline is obtained.

TABLE 7

| Solution | # of Injections | Gradient |
| --- | --- | --- |
| Blank Solution | 1* | A |
| 0.1% Standard Solution (System Sensitivity) | 1 | B |

TABLE 7-continued

| Solution | # of Injections | Gradient |
| --- | --- | --- |
| 0.20% Standard Solution | 5 | B |
| 0.60% Standard Solution | 1 | B |
| 1.0% Standard Solution | 1 | B |
| 1.6% Standard Solution | 1 | B |
| 2.0% Standard Solution | 1 | B |
| 0.20% Standard Solution Check | 1 | B |
| Test Sample Solution Prep A | 1 | A |
| Test Sample Solution Prep B | 1 | A |
| 0.20% Standard Solution Check | 1 | B |

Additional test sample injections may be added as required. No more than 6 test sample solution injections are to be performed before repeating the 0.20% standard solution check injection.

For evaluation, all peaks should be integrated associated with any unknown impurities detected. If baseline noise is an issue, make sure that the waste is properly drained from the detector. It may be necessary to check that there is no liquid accumulated inside the tubing draining the waste from the ELSD. The tubing position should be corrected as needed. If the waste is being properly drained and the baseline noise is an issue, the detector may be cleaned. If required, the following cleaning method may be used prior to analysis. For cleaning, the HPLC conditions are as follows: The column is to be removed from the instrument and a union is to be used. The mobile phase is 100% $H_2O$ (isocratic 100%). The flow rate is 1.0 mL per minute. The column temperature is ambient temperature. The run time is 60 minutes. The ELSD operating conditions are as follows: The gain is 50. The drift tube temperature is 100° C. The gas pressure (nitrogen) is 50 PSI. The nebulizer is set to heating at 75%.

Typical retention times are shown in Table 8. In Table 8, "DAG" is dianhydrogalactitol. DAG in the test sample is not quantitated in this method. DAG is observed as a wide peak due to the concentration of DAG required. Retention time for DAG in sample solution is approximately between 10 and 13 minutes.

TABLE 8

| Component | RT, min | RRT |
| --- | --- | --- |
| Dulcitol | 6.4 | 0.53 |
| * DAG | 12.1* | 1.00 |

Figure 6:
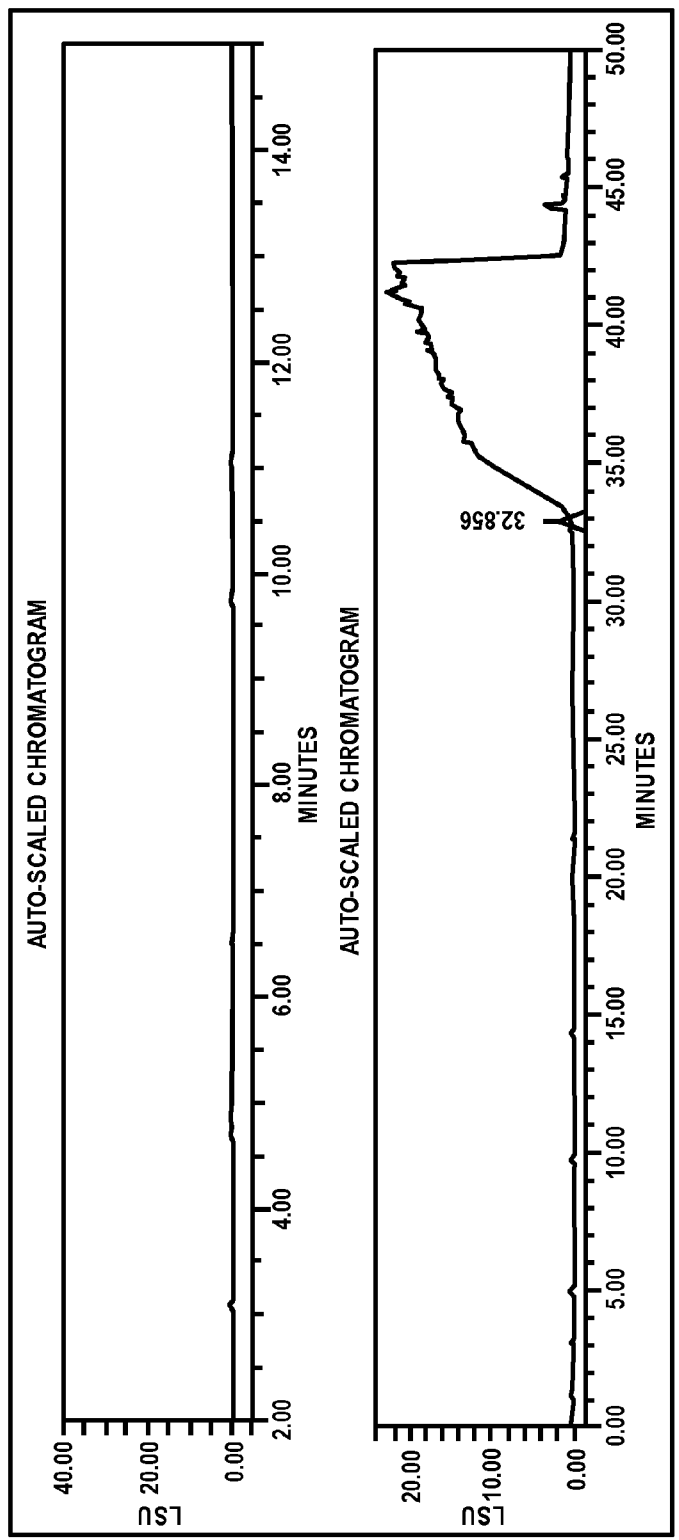
FIG. 6 is an example chromatogram of a blank solution as performed in Example 4.

FIG. 6 is an example chromatogram of a blank solution.

Figure 7:
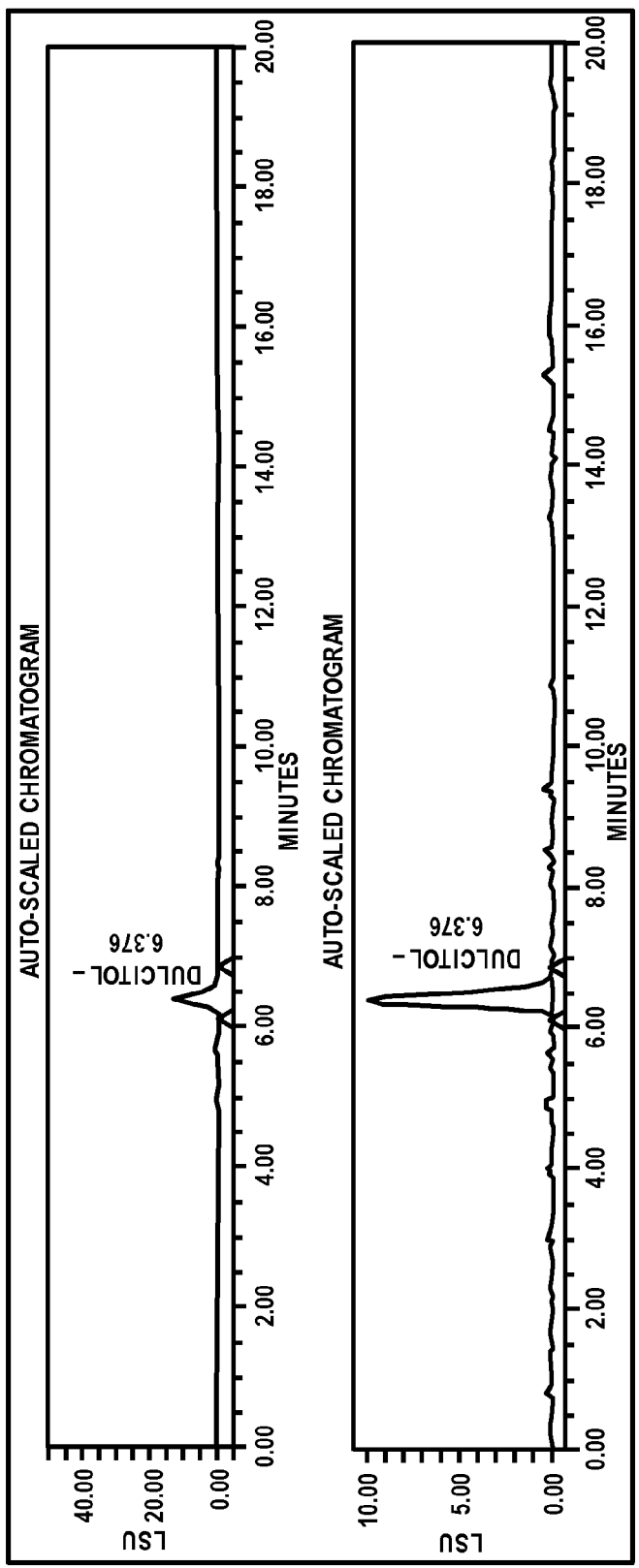
FIG. 7 is an example chromatogram of an 0.10% dulcitol solution as performed in Example 4.

FIG. 7 is an example chromatogram of 0.10% standard solution (system sensitivity solution).

Figure 8:
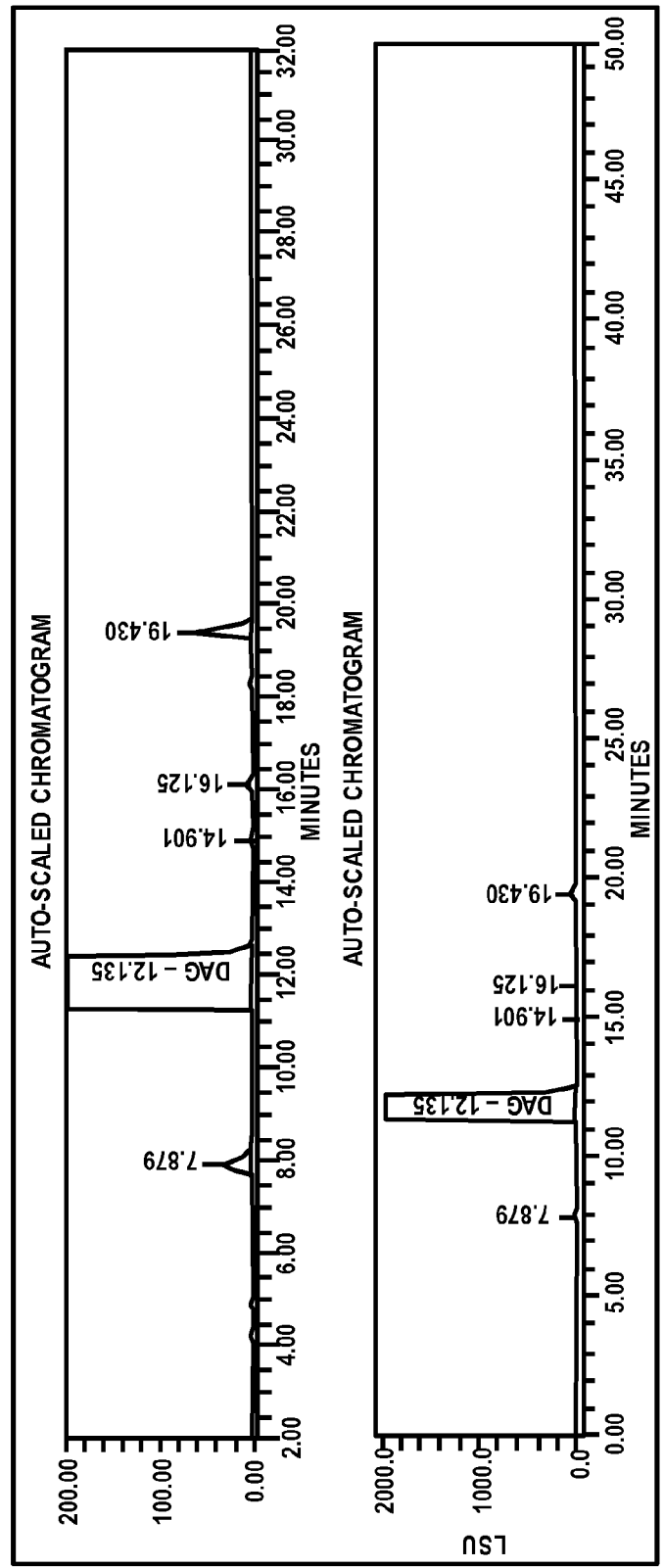
FIG. 8 is an example chromatogram of a test solution as performed in Example 4.

FIG. 8 is an example chromatogram of a test solution.

System suitability requirements are as follows. For blank solution injection, no interfering peaks should be observed at the retention time of the dulcitol peak or of any known impurities. A stable and reproducible baseline should be observed; continue to inject the blank solution until this condition is met. For system sensitivity, the dulcitol peak subsequent to the injection of the 0.10% standard solution should be observed. The signal-to-noise ratio for the dulcitol peak should be reported. If contamination in the mobile phase is suspected (i.e., baseline noise is greater than 1.0 LSU) or the dulcitol peak is not observed, the mobile phase should be re-prepared or the clean-up procedure described above should be performed. The USP tailing factor for the dulcitol peak for the first and last injections of the 0.20% standard solution is no more than 2.0. For precision, the % RSD for the log of peak area in the five injections is calculated. The % RSD must be no more than 15%.

For calculations, all peaks that are not attributed to the blank should be integrated. The logarithm of the response versus the logarithm of the concentration for the 0.10% through the 2.0% standard solutions for dulcitol (including the 5 precision injections of the 0.20% standard) is plotted. The correlation coefficient (r) must be no less than 0.98 for the linearity curve. The slope and intercept are determined from the curve. The linearity curve for dulcitol is used to determine the concentration in mg/mL of unknowns and dulcitol impurities in the sample.

For determination of individual unknown impurities in the sample, the slope and intercept from the linearity curve for dulcitol as described above are used. Using the Log [area response] of the Unknown, the Log [concentration] of the unknown is determined as follows using Equation (1):

$$\text{Log[Unknown concentration]} = \frac{\text{Log[Unknown response]} - \text{Intercept}}{\text{Slope}}. \quad (1)$$

The amount of unknown impurity (in mg/mL) is determined as follows using Equation (2):

$$\text{Unknown concentration (mg/mL)} = 10^{Log\,[Unknown\,concentration]} \quad (2).$$

The percentage of each unknown impurity is determined as follows using Equation (3):

$$\%\,\text{Unknown} = \frac{\text{Unknown concentration(mg/mL)} \times 100}{\text{Spl. Conc. (mg/mL)}}. \quad (3)$$

Alternatively, quantitation using dulcitol standards may be formed using log-log linear function in Empower (Waters Corp.)

Similar equations, specifically Equations (4)-(6), are used for the determination of the dulcitol impurity in the sample.

Using the log [area response] for dulcitol, the log [concentration] of dulcitol is determined using Equation (4):

$$\text{Log[Dulcitol concentration]} = \frac{\text{Log[Dulcitol response]} - \text{Intercept}}{\text{Slope}}. \quad (4)$$

The concentration of dulcitol impurity (in mg/mL) is determined using Equation (5):

$$\text{Dulcitol concentration (mg/mL)} = 10^{Log\,[Dulcitol\,concentration]} \quad (5).$$

The percentage of dulcitol impurity is determined using Equation (6):

$$\%\,\text{Dulcitol} = \frac{\text{Dulcitol concentration(mg/mL)} \times 100}{\text{Spl. Conc.(mg/mL)}}. \quad (3)$$

Advantages of the Invention

The present invention provides an improved analytical method for the detection and quantitation of impurities present in dianhydrogalactitol preparations, including dulcitol and unknown impurities, as well as methods for isolation and identification of unknown impurities present in dianhydrogalactitol preparations. The methods of the present invention allow the large-scale preparation of dianhydrogalactitol of high purity suitable for pharmaceutical use and reduce the possibility of significant side effects caused by the presence of impurities in dianhydrogalactitol preparations intended for pharmaceutical use.

Methods according to the present invention possess industrial applicability for analysis of dianhydrogalactitol preparations and determination and quantitation of impurities in dianhydrogalactitol preparations.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, and literature references, as well as those publications that have been incorporated in those published documents. However, to the extent that any publication incorporated herein by reference refers to information to be published, applicants do not admit that any such information published after the filing date of this application to be prior art.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

What is claimed is:

1. An analytical method for analyzing the presence and quantity of impurities present in a preparation of dianhydrogalactitol comprising the step of:
analyzing a preparation of dianhydrogalactitol by subjecting the preparation to high performance liquid chromatography (HPLC) on an HPLC column using elution with a mobile phase gradient to separate dianhydrogalactitol from dulcitol and other contaminants of the preparation,
wherein the HPLC column is a silica gel column bonded to C 18 compounds and finished with an endcapping procedure employing Lewis acid-Lewis base chemistry,
wherein the mobile phase gradient comprises Mobile Phase A and Mobile Phase B, with Mobile Phase A being 0.05% formic acid in water and Mobile Phase B being 100% methanol,
wherein a first elution sequence is performed with a gradient of 95% water/5% acetonitrile to 70% water/30% acetonitrile, returning to 95% water/5% acetonitrile,
wherein following the first elution sequence, a second elution sequence is performed as follows: from 0 minutes to 7.5 minutes with 100% of 0.05% formic acid; from 7.5 minutes to 7.6 minutes with 97% of 0.05% formic acid and 3% of methanol; and from 7.6 minutes to 20 minutes with 100% of 0.05% formic acid, and
wherein the high performance liquid chromatography employs evaporative light scattering detection (ELSD).

2. The analytical method of claim 1 wherein a time schedule for varying the first elution sequence is as follows: 0 minutes, 95% water/5% acetonitrile; 15 minutes, 95% water/5% acetonitrile; 15.1 minutes, 70% water/30% acetonitrile; 20 minutes, 70% water/30% acetonitrile; 20.1 to 35 minutes, 95% water/5% acetonitrile.

3. The analytical method of claim 1 wherein the method detects a monoepoxide degradation product of dianhydrogalactitol, a monoepoxide dimer, and dulcitol.

4. The analytical method of claim 3 wherein the method also detects a dimer of dianhydrogalactitol and condensed products.

5. The analytical method of claim 1 wherein the peaks resulting from HPLC are analysed by LC-MS.

6. The analytical method of claim 1 wherein the method further comprises a step of determining the relative concentration of one or more peaks resolved by high performance liquid chromatography that represent compounds other than dianhydrogalactitol itself.

7. The analytical method of claim 1 wherein the column temperature is about 30° C.

8. The analytical method of claim 1 wherein the flow rate of the mobile phase gradient is about 0.5 mL/min.

9. The analytical method of claim 1 wherein the ELSD detector is operated in cooling mode with the drift tube temperature of 35° C. and gain 400, 2 pps, 45 PSI.

10. The analytical method of claim 1 wherein the first elution sequence is performed from 0 minutes to 25 minutes with 100% of 0.05% formic acid in water, from 25 minutes to 25.1 minutes with 90% of 0.05% formic acid in water and 10% of 100% methanol, from 25.1 minutes to 35 minutes with 10% of 0.05% formic acid in water and 90% of 100% methanol, and from 35.1 minutes to 50 minutes with 100% of 0.05% formic acid in water.

11. The analytical method of claim 1 wherein the method further comprises the preparation of an external calibration standard curve for an impurity.

12. The analytical method of claim 10 wherein the method further comprises the preparation of an external calibration standard curve for an impurity.

13. The analytical method of claim 11 wherein the impurity is selected from the group consisting of dulcitol, a monoepoxide degradation product of dianhydrogalactitol, and a dimer of dianhydrogalactitol.

14. The analytical method of claim 12 wherein the impurity is selected from the group consisting of dulcitol, a monoepoxide degradation product of dianhydrogalactitol, and a dimer of dianhydrogalactitol.

15. The analytical method of claim 1 wherein, for an unknown impurity, the content of the unknown impurity is estimated using a calibration standard curve established by chromatography of dianhydrogalactitol reference material.

16. The analytical method of claim 1 wherein, for an unknown impurity, the content of the unknown impurity is estimated using a calibration standard curve established by chromatography of dianhydrogalactitol reference material.

17. The analytical of claim 1 wherein the column temperature for HPLC is about 30° C., the sample temperature for HPLC is about 5° C., the flow rate for HPLC is about 0.5 mL/min, and the injection volume is about 10-100 μL.

18. The analytical method of claim 1 wherein, for ELSD, the gain is about 400, the drift tube temperature is about 45° C., the gas pressure is about 35 PSI of nitrogen, the nebulizer is set to cooling, the data rate is 2 points per second, and the Rayleigh factor is about 6.0.

19. The analytical method of claim 1 wherein standards of 2.0% dulcitol, 1.6% dulcitol, 1.0% dulcitol, 0.60% dulcitol, 0.20% dulcitol, and 0.10% dulcitol are employed to determine the sensitivity and linearity of the system.

20. The analytical method of claim 1 wherein the retention time for dulcitol is about 6.4 minutes and the retention time for dianhydrogalactitol is about 12.1 minutes.

21. The analytical method of claim 1 wherein the amount and percentage of a dulcitol impurity are determined from the results of HPLC and ELSD.

22. The analytical method of claim 1 wherein the amount and percentage of an unknown impurity other than dulcitol are determined from the results of HPLC and ELSD.

* * * * *